United States Patent
Lin et al.

(10) Patent No.: US 6,708,565 B2
(45) Date of Patent: Mar. 23, 2004

(54) ULTRASONIC WAFER BLADE VIBRATION DETECTING

(75) Inventors: Chein-Fang Lin, Pingtung (TW); Jeng-Yann Tsay, Tainan (TW); Chih-Pen Yen, Kaohusiung (TW); Yong-Mao Hsu, Tainan (TW)

(73) Assignee: Taiwan Semiconductor Manufacturing Co., Ltd., Hsin Chu (TW)

( * ) Notice: Subject to any disclaimer, the term of this patent is extended or adjusted under 35 U.S.C. 154(b) by 0 days.

(21) Appl. No.: 10/133,784

(22) Filed: Apr. 26, 2002

(65) Prior Publication Data

US 2003/0200808 A1 Oct. 30, 2003

(51) Int. Cl.[7] .......................... G01M 1/22; G01H 11/00
(52) U.S. Cl. ........................ 73/660; 702/56; 324/207.25
(58) Field of Search ........................ 73/593, 599, 597, 73/596, 598, 600, 660, 661, 658, 659; 702/56; 324/207.15, 207.16, 207.22, 207.25

(56) References Cited

U.S. PATENT DOCUMENTS

| | | | | |
|---|---|---|---|---|
| 4,518,917 A | * | 5/1985 | Oates et al. ................. 73/660 |
| 4,573,358 A | * | 3/1986 | Luongo ....................... 73/660 |
| 4,887,468 A | * | 12/1989 | McKendree et al. .......... 73/660 |
| 4,896,537 A | * | 1/1990 | Osborne ...................... 73/660 |
| 4,951,500 A | * | 8/1990 | Twerdochlib et al. ..... 73/119 R |
| 5,206,816 A | * | 4/1993 | Hill et al. .................... 73/660 |
| 5,996,415 A | * | 12/1999 | Stanke et al. ................. 73/597 |

* cited by examiner

Primary Examiner—Helen Kwok
(74) Attorney, Agent, or Firm—Tung & Associates

(57) ABSTRACT

Detecting blade vibration via ultrasonic waves is disclosed. The blade may be part of a robot that is used in conjunction with semiconductor device fabrication. A process chamber is provided that has a sidewall and a base defining a cavity contained therein. A rotatable blade is mounted at a center of the cavity that has a base portion and a tip portion extensible from the center to the sidewall of the process chamber. One or more ultrasonic sensors are mounted on the base adjacent to the sidewall. Ultrasonic waves are sent and received toward and reflected by the tip portion of the wafer blade to determine the tip portion's position. In this way, vibrational movement of the blade can be detected.

20 Claims, 4 Drawing Sheets

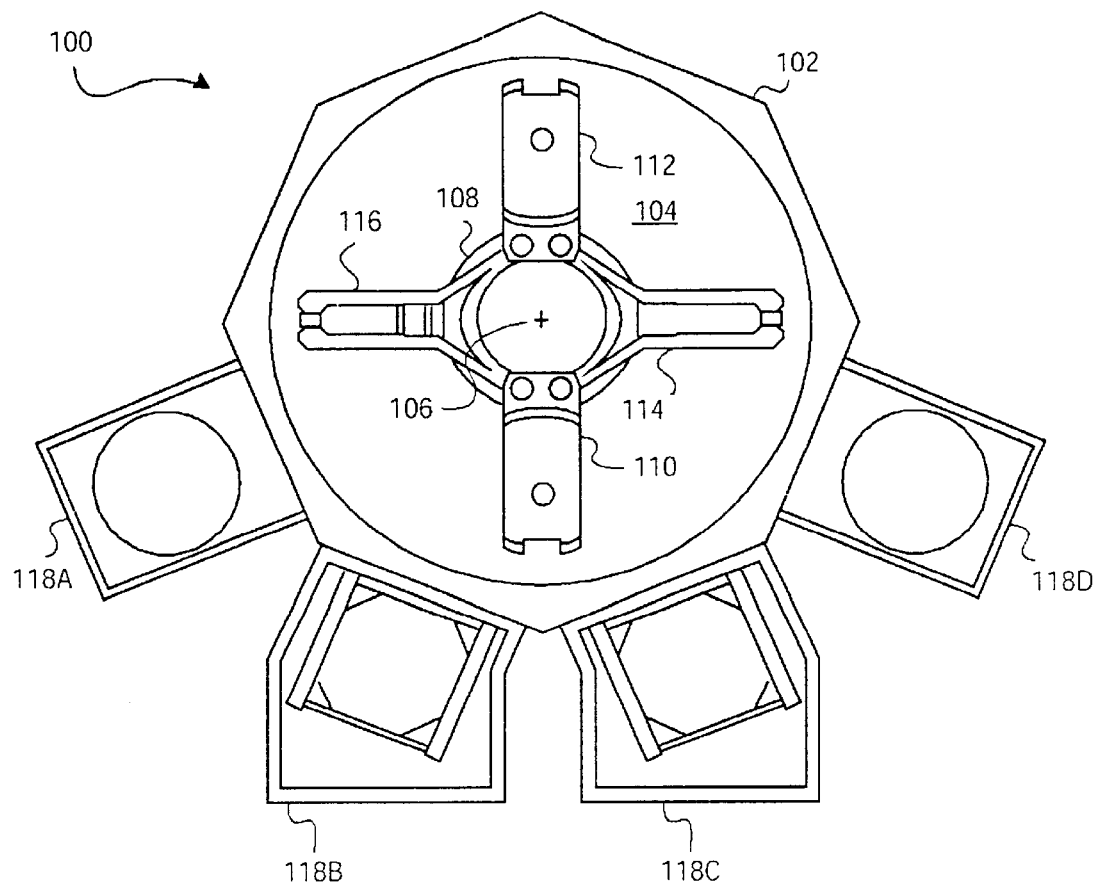
FIG. 1
*Prior Art*
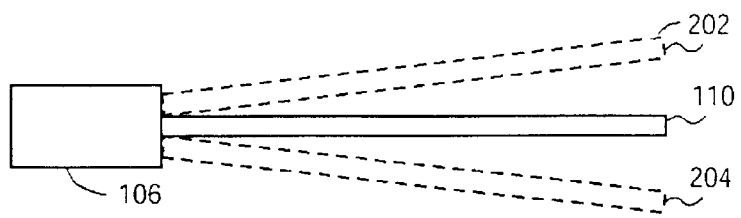
FIG. 2  *Prior Art*

ULTRASONIC WAFER BLADE VIBRATION DETECTING

FIELD OF THE INVENTION

This invention relates generally to rotating or spinning blades, such as may be found in robots used in conjunction with semiconductor fabrication equipment, and more particularly to detecting vibration of such blades.

BACKGROUND OF THE INVENTION

Robots are increasingly being used in many different applications, including semiconductor device fabrication. A robot can be generally and non-restrictively defined as a stand-alone hybrid computer system that performs physical and computational tasks. It is a multiple-motion device with one or more arms and that is capable of performing many different tasks. It can be designed similar to human form, although most industrial robots do not resemble people at all. Robots are used extensively in manufacturing, including semiconductor device fabrication.

FIG. 1 shows a robot 100 that is used in conjunction with semiconductor device fabrication. The robot 100 includes a process chamber 102, the sidewalls of which meet at a base at the bottom to form a cavity 104. A blade assembly 108 is positioned at the bottom of the base of the chamber 102, and rotates around an axis of rotation 106 at the center of the base of the chamber 102. The blade assembly 108 has a primary wafer blade 110, an auxiliary wafer blade 112, a straight wing 114, and an angled wing 116. The wafer blades 110 and 112 each have a base portion and a tip portion, the latter which is extensible from the center of the base of the chamber 102 to the sidewall of the chamber 102. The blade assembly 108 is used to transfer semiconductor wafers among different wafer orientation chambers, such as may include the chambers 118a, 118b, 118c, and 118d. The robot 100 may be a Centura robot as is available from Applied Materials, Inc., of Santa Clara, Calif.

A potential problem with the robot 100 is when the primary blade 110 begins to vibrate, moving up and down besides just rotating. This is shown in FIG. 2. From the center 106, the blade 110 should be located as is indicated in FIG. 2. However, when it vibrates, it moves up and down, from and to the positions 202 and 204. The vibration of the wafer blade 110 can have disadvantageous consequences. A semiconductor wafer may slide out, or may be damaged by the vibrating blade 110, since it is typically located only 1.5 millimeters from the blade 110. Furthermore, vibration may indicate that the robot 100 is becoming damaged, such as the bearings thereof that control the movement of the primary blade 110.

Therefore, there is a need for detecting blade vibration. Such blade vibration detection should ensure that semiconductor wafers are not damaged. Such blade vibration detection should also provide an early warning that the robot of which the blade is a part is becoming damaged. For these and other reasons, there is a need for the present invention.

SUMMARY OF THE INVENTION

The invention relates to detecting blade vibration via ultrasonic waves. The blade may be part of a robot that is used in conjunction with semiconductor device fabrication. A process chamber is provided that has a sidewall and a base defining a cavity contained therein. A rotatable blade is mounted at a center of the cavity that has a base portion and a tip portion extensible from the center to the sidewall of the process chamber. One or more ultrasonic sensors are mounted on the base adjacent to the sidewall. Ultrasonic waves are sent and received toward and reflected by the tip portion of the wafer blade to determine the tip portion's position. In this way, vibrational movement of the blade can be detected.

Embodiments of the invention provide for advantages over the prior art. If vibration exceeds specifications, then the blade can be stopped, or an operator can be notified that the blade should be stopped. This prevents damage to semiconductor wafers, as well as to the blade or the robot itself. Furthermore, detection of vibration provides an early warning that the robot may be becoming damaged, and thus should be investigated. Still other aspects, embodiments, and advantages of the invention will become apparent by reading the detailed description that follows, and by referring to the accompanying figures.

BRIEF DESCRIPTION OF THE DRAWINGS

FIG. 1 is a diagram of a robot having a wafer blade that may suffer from blade vibration, in conjunction with which embodiments of the invention may be practiced.

FIG. 2 is a diagram showing in detail how the wafer blade of the robot of FIG. 1 can undesirably vibrate.

DETAILED DESCRIPTION OF THE INVENTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

Figure 3:
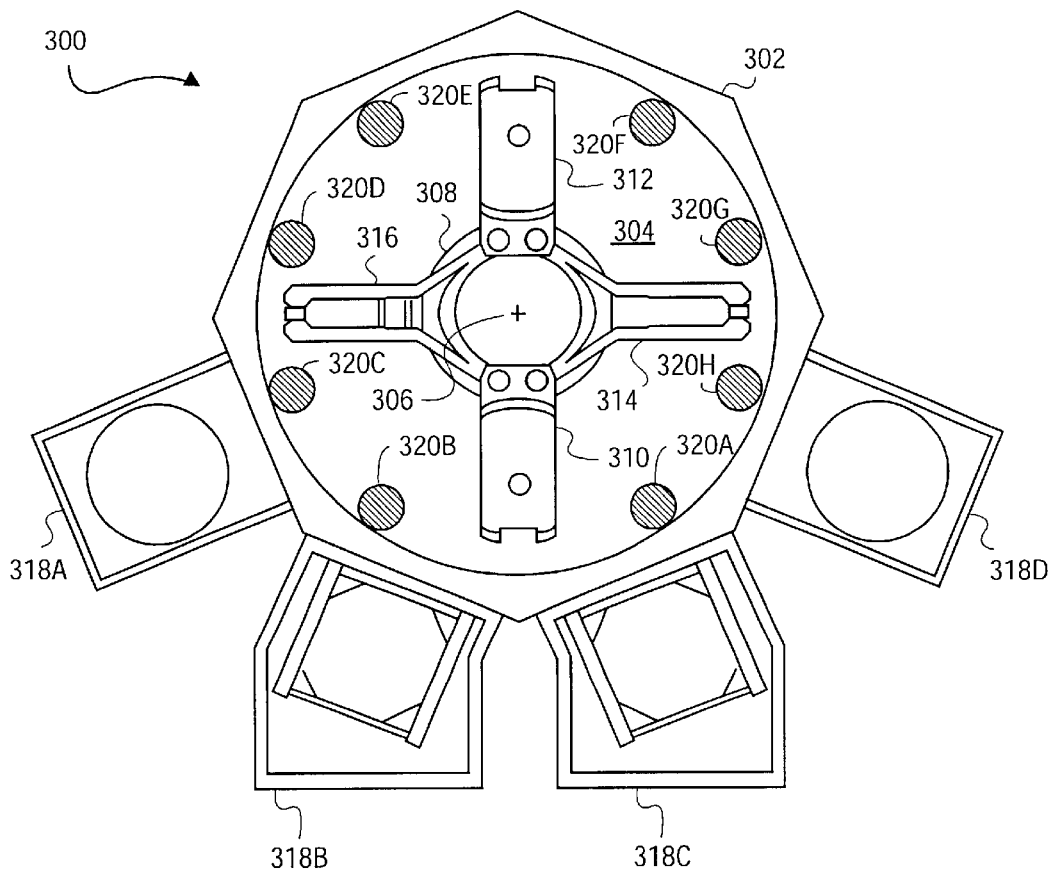
FIG. 3 is a diagram of a robot having a wafer blade and a number of ultrasonic sensors to detect vibration of the wafer blade, according to an embodiment of the invention. The embodiment of FIG. 3 is an example only, and is not meant to limit the applications in which the ultrasonic blade vibration detection according to the invention can be implemented.

FIG. 3 shows a robot 300 that is used in conjunction with semiconductor device fabrication. The robot 300 includes a process chamber 302, the sidewalls of which meet at a base at the bottom to form a cavity 304. A blade assembly 308 is positioned at the bottom of the base of the chamber 302, and rotates around an axis of rotation 306 at the center of the base of the chamber 302. The blade assembly 308 has a primary wafer blade 310, an auxiliary wafer blade 312, a straight wing 314, and an angled wing 316. The wafer blades 310 and 312 each have a base portion and a tip portion, the latter which is extensible from the center of the base of the chamber 302 to the sidewall of the chamber 302. The blade assembly 308 is used to transfer semiconductor wafers among different wafer orientation chambers, such as may include the chambers 318a, 318b, 318c, and 318d. The robot 300 may be a Centura robot as is available from Applied Materials, Inc., of Santa Clara, Calif.

To detect vibration of the blade 310, a number of ultrasonic sensors 320a, 320b, 320c, 320d, 320e, 320f, 320g, and 320h are positioned near the sidewall of the cavity 304 of the process chamber 302. There may be more or less of these ultrasonic sensors that the number indicated in FIG. 3. For instance, there may be as little as one ultrasonic sensor. In general, each ultrasonic sensor emits an ultrasonic wave that is reflected by the primary blade 310 as it rotates around the center 306 of the cavity 304. The ultrasonic wave is thus received back by the sensor. The time it takes for the ultrasonic wave to be received back, as measured from the time the wave was emitted, is used to determine the position of the blade 310. The position of the blade 310 thus can be compared with the position of the blade 310 as determined by other sensors, or at different times as determined by the same sensor, to determine if unacceptable, out-of-specification blade vibration is occurring.

Figure 4:
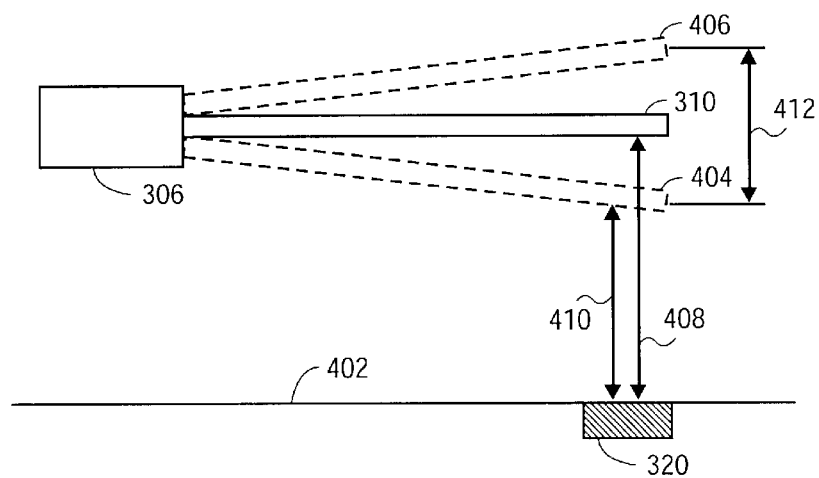
FIG. 4 is a diagram showing in detail how the wafer blade of the robot of FIG. 3 can undesirably vibrate, and how the ultrasonic sensors of FIG. 3 are used to detect such undesirable vibration, according to an embodiment of the invention.

FIG. 4 shows this detection of blade vibration in more detail. The blade 310 should be at the position indicated in FIG. 4, from the center 306. However, it may vibrate from and to positions 404 and 406. Thus, the ultrasonic sensor 320, mounted to the base 402 of the chamber 320 of FIG. 3, determines the position of the blade 310 as the distance 408. It may then determine the position of the blade 310 as the distance 410. From these two distances 408 and 410, it can be determined that the vibration is equal to the distance 412 between the positions 404 and 406. If this vibration is not less than (i.e., greater than) a given specification, then it is deemed an unacceptable vibration.

More particularly, the speed of the ultrasonic wave emitted by the ultrasonic sensor 320 is indicated as $V_s$. The wave is emitted at time $t_t$, and is received at time $t_r$. Therefore, the distance 408 is equal to $$d_1 = V_s \frac{(t_{r1} - t_{t1})}{2} \quad (1)$$

and the distance 410 is equal to $$d_2 = V_2 \frac{(t_{r2} - t_{t2})}{2} \quad (2)$$

Equations (1) and (2) can then be used to determined the distance 412 as $$\Delta d = 2(d_2 - d_1) = V_s[(t_{r1} - t_{t1}) - (t_{r2} - t_{t2})] = V_s \Delta t \quad (3)$$

Thus, the absolute difference between the recorded time for an ultrasonic wave to go from and to the sensor 320 a first time and the recorded time for another wave to go from and to the sensor 320 a second time, times the speed of the ultrasonic wave, is the vibration of the rotating blade.

Figure 5:
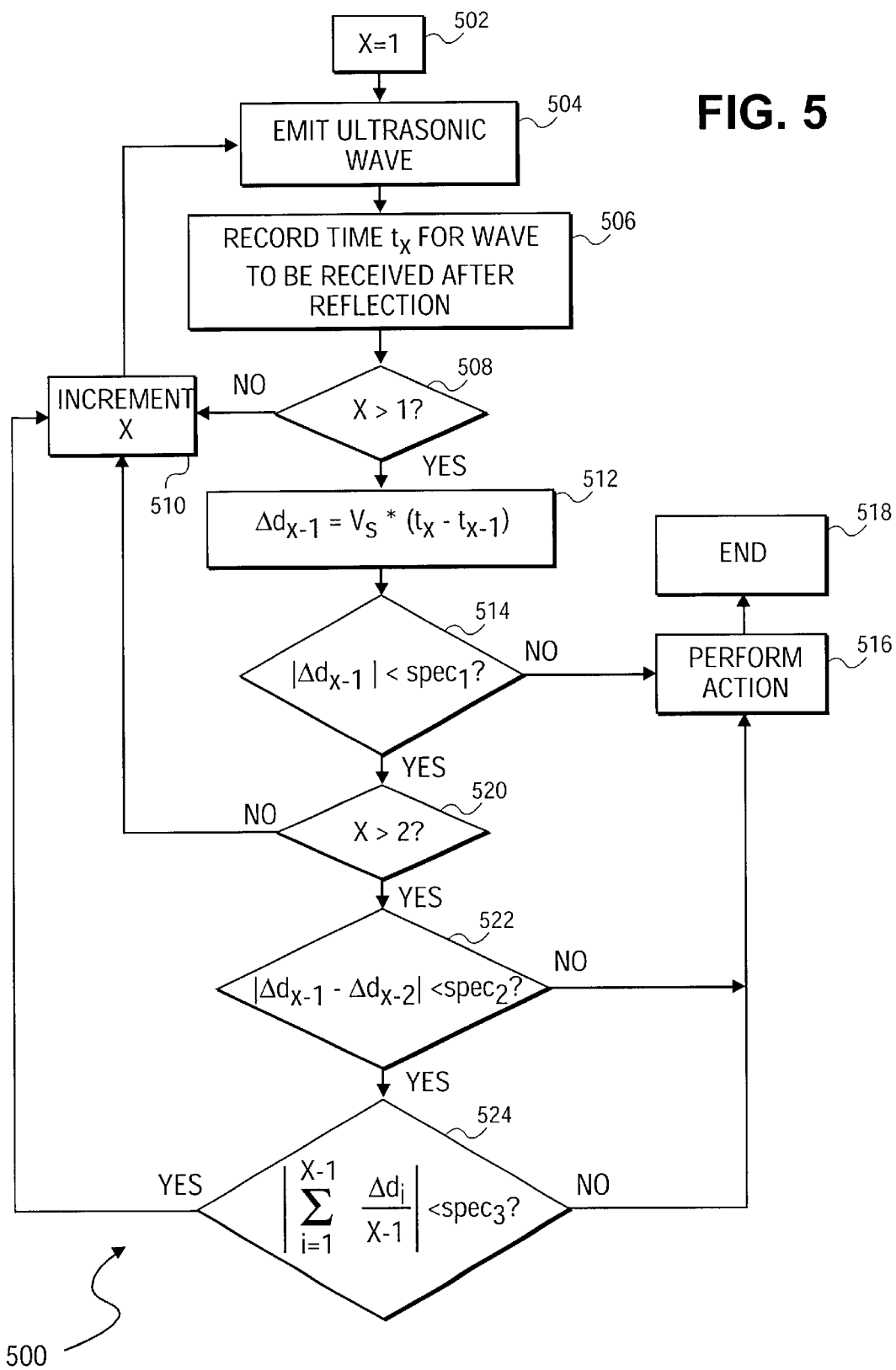
FIG. 5 is a flowchart of a method showing in detail how an ultrasonic sensor can be used to detect undesirable blade vibration, according to an embodiment of the invention. The method of FIG. 5 may be implemented in conjunction with the robot of FIG. 3 in one embodiment.

FIG. 5 shows a method 500 according to an embodiment of the invention for detecting blade vibration, and performing an action in response to such detection. First, a counter x is set to 1 (502). An ultrasonic wave is emitted by an ultrasonic sensor (504) that is reflected back by the rotating blade and detected by the ultrasonic sensor. The time it takes, $t_x$, for the wave to be received after its emittance and reflection, is recorded (506). If the counter x is not greater than one (508), then the counter x is incremented (510), and another ultrasonic wave is emitted (504), to record a new $t_x$ for the wave to be received.

Once the counter x is greater than one (508), then the vibration distance difference $Dd_{x-1}$ is determined as the speed of the ultrasonic wave, $V_s$, times the difference $t_x - t_{x-1}$ (512). If this vibration distance difference, absolutely, is not less than a first specification, such as one millimeter (514), then the vibration distance difference is out of specification and thus unacceptable, and an action is performed (516). The action may be stopping the blade from rotating, or indicating to an operator that unacceptable vibration of the blade is occurring. The method 500 is then finished (518).

However, if the vibration distance difference, absolutely, is less than a first specification (514), then the method 500 proceeds to determine whether the counter x is greater than two. If the counter x is not greater than two (520), then x is incremented (510), and 504, 506, 508, 512, and 514 are performed again. Once the counter x is greater than two (520), then it is determined whether the current vibration distance difference determined, $Dd_{x-1}$, minus the previous vibration distance difference determined, $Dd_{x-2}$, absolutely is less than a second specification, such as 0.5 millimeter (522). If this absolute difference is not less than the second specification (522), then the vibration is out of specification and thus unacceptable, and an action is performed (516). The method 500 is then finished (518).

Otherwise, if this absolute difference is less than the second specification (522), then the method 500 proceeds to determine whether the average vibration distance difference is less than a third specification (524). If the average vibration distance difference is not less than the third specification (524), then the vibration is out of specification and unacceptable, and the method 500 again performs an action (516), and the method 500 is finished (518). If the average vibration distance is less than the third specification (524), then x is again incremented (510), and the method 500 repeats as has been previously described, by emitting another ultrasonic wave in 504.

Figure 6:
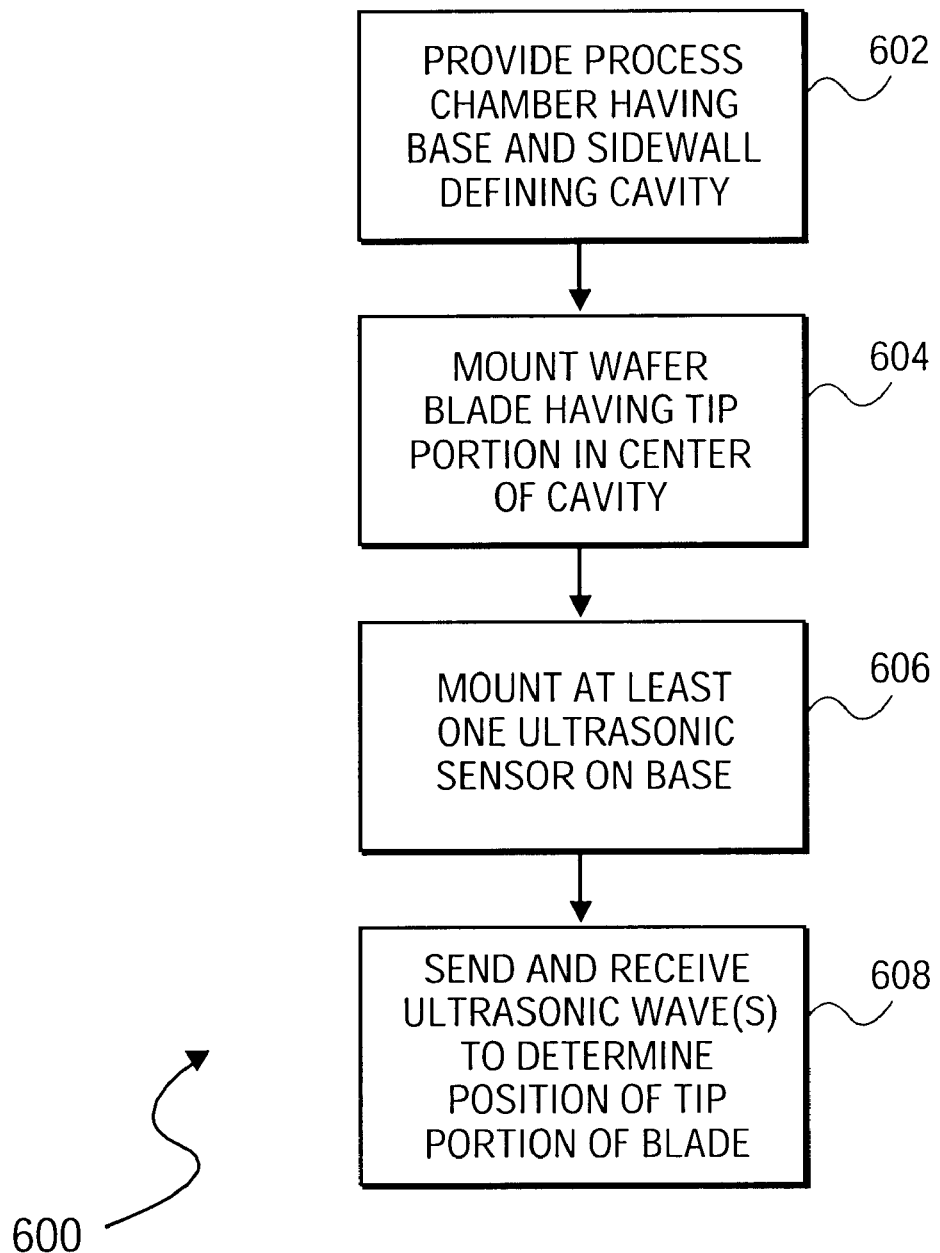
FIG. 6 is a flowchart of a method outlining how one embodiment of the invention provides for ultrasonic blade vibration detection, and is consistent with the embodiments of FIGS. 3, 4, and 5.

Finally, FIG. 6 shows a method 600 that outlines the approach for ultrasonic blade vibration detection according to an embodiment of the invention. A process chamber having a sidewall and a base that define a cavity contained therein is provided (602). A rotatable wafer blade is mounted at the cavity's center (604). The wafer blade has a base portion and a tip portion extending from the center to the sidewall of the chamber. At least one ultrasonic sensor is mounted on the base of the chamber adjacent the sidewall (606). Ultrasonic waves are then sent and received, as reflected by the blade, by the ultrasonic sensor to determine the position of the tip portion of the blade (608), and hence whether the blade is undesirably vibrating.

It is noted that, although specific embodiments have been illustrated and described herein, it will be appreciated by those of ordinary skill in the art that any arrangement is calculated to achieve the same purpose may be substituted for the specific embodiments shown. This application is intended to cover any adaptations or variations of the present invention. For instance, whereas the invention has been substantially described in relation to a particular robot having a particular blade configuration, the invention itself is not so limited, and can be applied to other types of blades, within robots or other types of situations, and for purposes other than in conjunction with semiconductor fabrication. Therefore, it is manifestly intended that this invention be limited only by the claims and equivalents thereof.

What is claimed is:

1. A method for detecting vibrational movement of a wafer blade comprising:

providing a process chamber having a sidewall and a base defining a cavity contained therein;

mounting a rotatable wafer blade at a center of the cavity, the wafer blade having a base portion and a tip portion extensible from the center to the sidewall of the process chamber;

mounting at least one ultrasonic sensor on the base adjacent to the sidewall; and, sending and receiving an ultrasonic wave toward and reflected by the tip portion of the wafer blade to determine a position of the tip portion of the wafer blade relative to the base to determine vibrational movement of the blade.

2. The method of claim 1, further comprising:

sending and receiving a second ultrasonic wave toward and reflected by the tip portion of the wafer blade to determine a second position of the tip portion of the wafer blade; and, comparing the position of the tip portion of the wafer blade with the second position of the tip portion of the wafer blade.

3. The method of claim 1, further comprising:

sending and receiving at least one additional ultrasonic wave toward and reflected by the tip portion of the wafer blade to determine at least one additional position of the tip portion of the wafer blade; and, comparing the position of the tip portion of the wafer blade with the at least one additional position of the tip portion of the wafer blade.

4. The method of claim 1, wherein the wafer blade is used in conjunction with semiconductor device fabrication.

5. The method of claim 1, wherein the wafer blade is used to transfer a semiconductor wafer from one position to another position.

6. A method comprising:

emitting a first ultrasonic wave by an ultrasonic sensor perpendicular to rotational movement of a rotating blade, reflected by the rotating blade back to the ultrasonic sensor for receipt thereby;

measuring a first time when the first ultrasonic wave was received back by the ultrasonic sensor compared to when the first ultrasonic wave was emitted by the ultrasonic sensor;

emitting a second ultrasonic wave by the ultrasonic sensor perpendicular to rotational movement of the rotating blade, reflected by the rotating blade back to the ultrasonic sensor for receipt thereby;

measuring a second time when the second ultrasonic wave was received back by the ultrasonic sensor compared to when the second ultrasonic wave was emitted by the ultrasonic sensor;

determining a vibration distance difference of the rotating blade as an ultrasonic wave speed times an absolute difference between the first time and the second time; and, in response to determining that the vibration distance difference is greater than a specified difference, performing an action relative to the rotating blade.

7. The method of claim 6, wherein performing the action relative to the rotating blade comprises stopping the rotating blade from rotating.

8. The method of claim 6, wherein performing the action relative to the rotating blade comprises instructing an operator to stop the rotating blade from rotating.

9. The method of claim 6, further comprising:

emitting a third ultrasonic wave by the ultrasonic sensor, reflected by the rotating blade back to the ultrasonic sensor for receipt thereby;

measuring a third time when the third ultrasonic wave was received back by the ultrasonic sensor compared to when the third ultrasonic wave was emitted by the ultrasonic sensor;

emitting a fourth ultrasonic wave by an ultrasonic sensor, reflected by the rotating blade back to the ultrasonic sensor for receipt thereby;

measuring a fourth time when the fourth ultrasonic wave was received back by the ultrasonic sensor compared to when the fourth ultrasonic wave was emitted by the ultrasonic sensor;

determining a second vibration distance difference of the rotating blade as the ultrasonic wave speed times an absolute difference between the third time and the fourth time; and, in response to determining that the second vibration distance difference is greater than the specified difference, performing the action relative to the rotating blade.

10. The method of claim 9, further comprising, in response to determining that an absolute difference between the vibration distance difference and the second vibration distance difference is greater than a second specified difference, performing the action relative to the rotating blade.

11. The method of claim 6, further comprising:

emitting a third ultrasonic wave by the ultrasonic sensor, reflected by the rotating blade back to the ultrasonic sensor for receipt thereby;

measuring a third time when the third ultrasonic wave was received back by the ultrasonic sensor compared to when the third ultrasonic wave was emitted by the ultrasonic sensor;

determining a second vibration distance difference of the rotating blade as the ultrasonic wave speed times an absolute difference between the third time and the second time; and, in response to determining that the second vibration distance difference is greater than the specified difference, performing the action relative to the rotating blade.

12. The method of claim 11, further comprising, in response to determining that an absolute difference between the vibration distance difference and the second vibration distance difference is greater than a second specified difference, performing the action relative to the rotating blade.

13. The method of claim 11, further comprising:

emitting a fourth ultrasonic wave by an ultrasonic sensor, reflected by the rotating blade back to the ultrasonic sensor for receipt thereby;

measuring a fourth time when the fourth ultrasonic wave was received back by the ultrasonic sensor compared to when the fourth ultrasonic wave was emitted by the ultrasonic sensor;

determining a third vibration distance difference of the rotation blade as the ultrasonic wave speed times an absolute difference between the third time and the fourth time; and, in response to determining that the third vibration distance difference is greater than the specified difference, performing the action relative to the rotating blade.

14. The method of claim 13, further comprising, in response to determining that an absolute difference between the second vibration distance difference and the third vibration distance difference is greater than a second specified difference, performing the action relative to the rotating blade.

15. The method of claim 13, further comprising, in response to determining that an average vibration distance difference of the first vibration distance difference, the second vibration distance difference, and the third vibration distance difference, is greater than a third specified difference, performing the action relative to the rotating blade.

16. The method of claim 6, wherein the rotating blade is used in conjunction with a robot.

17. The method of claim 6, wherein the rotating blade is used to transfer a semiconductor wafer from one position to another position.

18. A system comprising:

a process chamber having a sidewall and a base defining a cavity contained therein;

a blade at a center of the cavity having a base portion and a tip portion extensible from the center to the sidewall of the process chamber and rotating around an axis of rotation at the center of the cavity; and, at least one ultrasonic sensor on the base of the cavity adjacent to the sidewall of the cavity to send and receive one or more ultrasonic waves toward and reflected from the tip portion of the blade to determine whether the blade is vibrating undesirably based on a distance determined between the blade and the base portion.

19. The system of claim 18, wherein the blade is used in conjunction with a robot.

20. The method of claim 18, wherein the blade is used to transfer a semiconductor wafer from one position to another position.

* * * * *